United States Patent
Palu et al.

(10) Patent No.: US 8,574,642 B2
(45) Date of Patent: *Nov. 5, 2013

(54) **ANTIVIRAL *MORINDA CITRIFOLIA* L. BASED FORMULATIONS AND METHODS OF ADMINISTRATION**

(75) Inventors: Afa Kehaati Palu, American Fork, UT (US); Chen Su, West Jordan, UT (US); Bing-Nan Zhou, Sandy, UT (US); Brett West, Orem, UT (US); Claude Jarake Jensen, Cedar Hills, UT (US); Stephen Story, Alpine, UT (US)

(73) Assignee: Tahitian Noni International, Inc., Provo, UT (US)

( * ) Notice: Subject to any disclaimer, the term of this patent is extended or adjusted under 35 U.S.C. 154(b) by 226 days.

This patent is subject to a terminal disclaimer.

(21) Appl. No.: 11/562,224

(22) Filed: Nov. 21, 2006

(65) Prior Publication Data
US 2007/0154580 A1     Jul. 5, 2007

Related U.S. Application Data

(60) Continuation-in-part of application No. 10/006,014, filed on Dec. 4, 2001, now abandoned, and a continuation-in-part of application No. 10/993,883, filed on Nov. 19, 2004, now Pat. No. 7,186,422, which is a division of application No. 10/286,167, filed on Nov. 1, 2002, now Pat. No. 6,855,345.

(60) Provisional application No. 60/740,593, filed on Nov. 29, 2005, provisional application No. 60/251,416, filed on Dec. 5, 2000, provisional application No. 60/335,313, filed on Nov. 2, 2001.

(51) Int. Cl.
*A61K 36/00*     (2006.01)

(52) U.S. Cl.
USPC .......................................... 424/777; 424/725

(58) Field of Classification Search
USPC .................................................. 424/725, 777
See application file for complete search history.

(56) References Cited

U.S. PATENT DOCUMENTS

| | | | |
|---|---|---|---|
| 4,039,559 | A | 8/1977 | Nakamura |
| 4,409,144 | A | 10/1983 | Heinicke |
| 4,463,025 | A | 7/1984 | Strobel |
| 4,543,212 | A | 9/1985 | Heinicke |

(Continued)

FOREIGN PATENT DOCUMENTS

| | | |
|---|---|---|
| CN | 1093919 | 10/1994 |
| CN | 1101256 | 4/1995 |

(Continued)

OTHER PUBLICATIONS

Navarre, I. :76 Ways to Use Noni Fruit Juice for Your Better Health; 2001, Pride Publishing, Vineyard, Utah; pp. 3-4, 115-116 and 119-124.*

(Continued)

*Primary Examiner* — Patricia Leith
(74) *Attorney, Agent, or Firm* — Michael F. Krieger; Kirton McConkie

(57) ABSTRACT

The present invention relates to methods and formulations directed to the management of Cathepsin G, Cathepsin S, Cathepsin B, Cathepsin L, Butyryl Cholinesterase, Peptidase HIV-1, and NF-kB enzymes comprising the administration of processed *Morinda citrifolia* based formulations.

6 Claims, 8 Drawing Sheets

(56) References Cited

U.S. PATENT DOCUMENTS

| | | |
|---|---|---|
| 4,666,606 A | 5/1987 | Heinicke et al. |
| 4,708,964 A | 11/1987 | Allen |
| 4,793,991 A | 12/1988 | Slimak |
| 4,948,785 A | 8/1990 | Nguyen |
| 4,996,051 A | 2/1991 | Meer et al. |
| 5,071,878 A | 12/1991 | Herschler |
| 5,106,634 A | 4/1992 | Thacker et al. |
| 5,110,803 A | 5/1992 | Nguyen |
| 5,213,836 A | 5/1993 | McGillivray et al. |
| 5,268,467 A | 12/1993 | Verbiscar |
| 5,275,834 A | 1/1994 | Thibault et al. |
| 5,288,491 A | 2/1994 | Moniz |
| 5,431,927 A | 7/1995 | Hand et al. |
| 5,472,699 A | 12/1995 | Duffy et al. |
| 5,503,825 A | 4/1996 | Lane |
| 5,565,435 A | 10/1996 | Yoneyama |
| 5,595,756 A | 1/1997 | Bally et al. |
| 5,616,569 A | 4/1997 | Reinhart |
| 5,717,860 A | 2/1998 | Graber et al. |
| 5,725,875 A | 3/1998 | Noll et al. |
| 5,731,356 A | 3/1998 | Jones et al. |
| 5,736,174 A | 4/1998 | Cooper et al. |
| 5,744,187 A | 4/1998 | Gaynor |
| 5,770,217 A | 6/1998 | Kutilek, III et al. |
| 5,776,441 A | 7/1998 | Scancarella et al. |
| 5,843,499 A | 12/1998 | Moreau et al. |
| 5,851,573 A | 12/1998 | Lepine et al. |
| 5,922,766 A | 7/1999 | Acosta et al. |
| 5,961,998 A | 10/1999 | Arnaud et al. |
| 5,962,043 A | 10/1999 | Jones et al. |
| 5,976,549 A | 11/1999 | Lewandowski |
| 6,029,141 A | 2/2000 | Bezos et al. |
| 6,039,952 A | 3/2000 | Sunvold et al. |
| 6,086,859 A | 7/2000 | Calello et al. |
| 6,086,910 A | 7/2000 | Howard et al. |
| 6,133,323 A | 10/2000 | Hayek |
| 6,136,301 A | 10/2000 | Pelle et al. |
| 6,139,897 A | 10/2000 | Goto et al. |
| 6,156,355 A | 12/2000 | Shields, Jr. et al. |
| 6,214,351 B1 | 4/2001 | Wadsworth et al. |
| 6,254,913 B1 | 7/2001 | Wadsworth et al. |
| 6,261,566 B1 | 7/2001 | Pillai et al. |
| 6,280,751 B1 | 8/2001 | Fletcher et al. |
| 6,291,533 B1 | 9/2001 | Fleischner |
| 6,299,925 B1 | 10/2001 | Xiong et al. |
| 6,387,370 B1 | 5/2002 | Yegorva |
| 6,405,948 B1 | 6/2002 | Hahn et al. |
| 6,417,157 B1 | 7/2002 | Wadsworth et al. |
| 6,436,449 B2 | 8/2002 | Gidlund |
| 6,477,509 B1 | 11/2002 | Hammons et al. |
| 6,528,106 B2 | 3/2003 | Wadsworth et al. |
| 6,589,514 B2 | 7/2003 | Jensen et al. |
| 6,737,089 B2 | 5/2004 | Wadsworth et al. |
| 6,749,875 B2 | 6/2004 | Selleck |
| 6,855,345 B2 | 2/2005 | Jensen et al. |
| 6,855,354 B2 | 2/2005 | Story et al. |
| 7,014,873 B2 | 3/2006 | West et al. |
| 7,018,662 B2 | 3/2006 | Jensen et al. |
| 7,033,624 B2 | 4/2006 | Jensen et al. |
| 7,048,952 B2 | 5/2006 | Gerson et al. |
| 7,070,813 B2 | 7/2006 | Jensen et al. |
| 7,122,211 B2 | 10/2006 | Jensen et al. |
| 7,144,439 B2 | 12/2006 | Isami |
| 7,186,422 B2 | 3/2007 | Jensen et al. |
| 2001/0033871 A1 | 10/2001 | Gidlund |
| 2002/0068102 A1 | 6/2002 | Su et al. |
| 2002/0090406 A1 | 7/2002 | Su et al. |
| 2002/0187168 A1 | 12/2002 | Jensen et al. |
| 2003/0060405 A1 | 3/2003 | Klieiman et al. |
| 2003/0086990 A1 | 5/2003 | Wang et al. |
| 2003/0108629 A1 | 6/2003 | Chou |
| 2003/0108630 A1 | 6/2003 | Story et al. |
| 2003/0108631 A1* | 6/2003 | Jensen et al. .......... 424/765 |
| 2003/0134001 A1 | 7/2003 | Jensen et al. |
| 2003/0134002 A1 | 7/2003 | Jensen et al. |
| 2003/0157205 A1 | 8/2003 | Jensen et al. |
| 2003/0206895 A1 | 11/2003 | Cavazza |
| 2003/0225005 A1 | 12/2003 | Gerson et al. |
| 2004/0086583 A1 | 5/2004 | Jensen et al. |
| 2004/0137094 A1* | 7/2004 | Mower et al. .......... 424/769 |
| 2004/0191341 A1 | 9/2004 | Palu et al. |
| 2004/0192761 A1 | 9/2004 | Palu et al. |
| 2004/0213862 A1 | 10/2004 | Su et al. |
| 2004/0224038 A1 | 11/2004 | Wang et al. |
| 2004/0244447 A1 | 12/2004 | Isami |
| 2004/0258780 A1 | 12/2004 | Woltering et al. |
| 2005/0037101 A1 | 2/2005 | Wang et al. |
| 2005/0075925 A1 | 4/2005 | Sash |
| 2005/0084551 A1 | 4/2005 | Jensen et al. |
| 2005/0106275 A1 | 5/2005 | Su et al. |
| 2005/0118291 A1 | 6/2005 | Wang et al. |
| 2005/0147700 A1 | 7/2005 | Jensen et al. |
| 2005/0158412 A1 | 7/2005 | Su et al. |
| 2005/0181082 A1 | 8/2005 | Isami et al. |
| 2005/0186296 A1 | 8/2005 | Palu et al. |
| 2005/0196476 A1 | 9/2005 | Zhou et al. |
| 2005/0202108 A1 | 9/2005 | Palu et al. |
| 2005/0202109 A1 | 9/2005 | Palu et al. |
| 2005/0260291 A1 | 11/2005 | Palu et al. |
| 2006/0088611 A1 | 4/2006 | Wang et al. |
| 2006/0141076 A1 | 6/2006 | Palu et al. |
| 2006/0159788 A1 | 7/2006 | West et al. |
| 2006/0193932 A1 | 8/2006 | Jensen et al. |
| 2006/0269630 A1 | 11/2006 | Palu et al. |
| 2006/0269631 A1 | 11/2006 | Su et al. |
| 2006/0275359 A1 | 12/2006 | Jensen et al. |
| 2006/0280818 A1 | 12/2006 | Palu et al. |
| 2007/0087066 A1 | 4/2007 | Gerson et al. |

FOREIGN PATENT DOCUMENTS

| | | |
|---|---|---|
| EP | 0555573 A1 | 8/1993 |
| EP | 0710450 A1 | 5/1996 |
| FR | 2673639 | 9/1992 |
| FR | 2783137 | 3/2000 |
| GB | 2253984 A | 9/1992 |
| JP | 355064504 | 5/1980 |
| JP | 61185167 | 8/1986 |
| JP | 62132829 | 6/1987 |
| JP | 06087736 | 3/1994 |
| JP | 06087737 | 3/1994 |
| JP | 8-208501 | 8/1996 |
| JP | 08208461 | 8/1996 |
| JP | 9-110688 | 4/1997 |
| JP | 11-43442 A | 2/1999 |
| JP | 2000095663 | 4/2000 |
| WO | 88/05304 A1 | 7/1988 |
| WO | 01/15551 A1 | 3/2001 |
| WO | 01/15553 A1 | 3/2001 |
| WO | 01/64231 A1 | 9/2001 |
| WO | 02/45654 A2 | 6/2002 |
| WO | 02/45734 A1 | 6/2002 |

OTHER PUBLICATIONS

Guardia et al. : Anti-Inflammatory Properties of Plant Flavonoids. Effects of Rutin, Quercetin and Hesperidin on Adjuvant Arthritis in Rat.: II Farmaco 56 (2001) pp. 683-687.*
Tierra. The Way of Herbs. Simon and Schuster. 1998. p. 171.*
Barney. Doctor's Guide to Natural Medicine: The Complete and Easy-To-Use-Natural Health Reference From a Medical Doctor's Perspective. Woodland Publishing. 1998. p. 70.*
Ng et al. Examination of Coumarins, Flavanoids and Polysaccharopeptide for Antibacterial Activity. Gen Pharmac. vol. 27. No. 7. pp. 1237-1240. 1996.*
Demrow et al. Administration of Wine and Grape Juice Inhibits in Vivo Platelet Activity and Thrombosis in Stenosed Canine Coronary Arteries. Circulation. 1995. pp. 1182-1188.*
Di Carlo et al. Flavanoids: Old and New Aspects of a Class of Natural Therapeutic Drugs. Life Sciences. vol. 60. No. 4. 1999. pp. 331-353.*
Daulataba et al., "Ricinoleic acid in *Morinda citrifolia* seed oil," J. Oil Tech. Assoc. India (Mumbai, India) 21 (2):26-27 (1989).

(56) References Cited

OTHER PUBLICATIONS

Dittmar, Morinda, "Use in Indigenous Samoan Medicine," J. of Herbs, Spices & Medicinal Plants, 1(3):77-92 (1993).

El-Gammal et al., "Antimicrobial Activities of Some Flavonoid Compounds," Microbiol. 141:561-565 (1986).

Elkins, Hawaiian Noni, Woodland Publishing, pp. 6-31 (1998).

Farine et al., "Volatile Components of Ripe Fruits of *Morinda citrifolia* and Their Effects on Drosophila", Phytochemistry, 1996, pp. 433-438, vol. 41, No. 2.

Gagnon, D., "Liquid Herbal Drops in Everyday Use," 3d Ed., Bot. Res. Ed. Inst., p. 27 (1997).

Gura, "Systems for Identifying New Drugs are Often Faulty," Science 278:1041-1042 (1997).

Hasegawa et al., "Anti-Helicobacter Pylor; Medicine Containing Extract of Dried Root of *Morinda citrifolia*," Abstract (1996).

Hirazumi et al.,"An Immunomodulatory Polysaccharide-Rich Substance from the Fruit Juice of *Morina citrifolia*(Noni) withAntitumorActivity,"Phytotherapy Research,13:380-387(1999).

Holleran, "The Zotics Splash, Beverage Industry," 91(6) (2000).

Lampur, "*Morinda* achieves phenomenal sales of Tahitian noni juice", Malaysian Nat. News Agency Jul. 1999, p. 1.

Kimstra et al., "Foods of the Key deer," FL Sci., 53(4):264-273 (1990).

Lane, "The Merck Manual," 17th Ed., pp. 449-451 (1999).

Levand et al., "Some chemical constituents of *Morinda citrifolia*," Planta Medica 36(2):186-187 (1979).

Liu et al., "2 Novel Glycosides from the Fruits of *Morinda citrifolia* (Noni) Inhibit AP-1 Transactivation & Cell Transformation in the Mouse Epidermal JB6 Cell Line," Cancer Res. 61:5749-5756 (2001).

Marona et al., "Pharmacological properties of some aminoalkanolic derivatives of xanthone," Pharmazie 56:567-572 (2001).

Morton, "The ocean-going noni, or Indian mulberry (*Morinda citrifolia*) and some of its 'colorful' relatives," Econ. Bot., 46(3):241-256 (192).

Mumford, L., "Benefits of Noni Juice may be Imagined; $30 Price Tag Isn't", So. Bend Tribune, So. Bend, Ind., pp. 1-2 (1998).

Naito, "Trace components in mulberry leaves," Nippon Nogei Kagaku Kaishi 42(7):423-425 (1968).

Peres et al., "Tetraoxygenated naturally occurring xanthones," Phytochemistry 55:683-710 (2000).

Product Alert. Oct. 11, 1999 29(19) PROMT Abstract.

Product Alert. Dec. 27, 1999 (29(24) PROMT Abstract.

Product Alert. Jun. 12, 2000 30(11) PROMT Abstract.

Rosenfeld, "Tropical Noni, a Tonic Boom; Nasty-Tasting Fruit Rockets onto the Health Product Market," Wash. Post; Aug. 7, 1997, p. C01:1-4 of Proquest.

Sang et al.,"Chemical Components in Noni Fruits and Leaves (*Morinda citrifolia* L.); Quality Management of Nutraceuticals,"Proceedings of Symposium,ACS,Wash.,DC pp. 134-150(2002.

"Rachel Perry Environmental Skin Protector SPF 18," Product Alert, V.29(2) (1999).

Tahitian Noni Products (http://www.noni-now.com) (1998-2003).

Terumo Corp., "Anti-helicobacter pylor; Medicine Containing Extract of dried roots of *Morinda citrifolia* . . ." Database DWPI on West, An. 1996-439483 JP 08-217686-Japan (Aug. 1996).

Wang et al., "Novel Trisaccharide Fatty Acid Ester Identified from the Fruits of *Morinda citrifolia* (Noni)" J. Agric. Food Chem. 47(12):4880-7882 (1999).

Webb, "Noni Juice Advice," Prevention Magazine-52:66 (2000).

Website publication: "A Pure Hawaiian Noni Juice," web.archive.org/web/20030523122956/http://www.nonialoha.com (2003).

Website publication: "Betterman" by Interceuticals, www.naturalhealtheconsultant.com/Monographs/Betterman.html (1998).

Website publication: "*Morinda*," www.drugdigest.org/DD/DV/HebsTake/0,3927,552025/Morinda.00.html (2003).

Website publication: "NONI in the News," www.incc.org/news-june.htm (2002).

Website publication: "NONI: Ugly but with a beautiful soul," www.web.archive.org/web/20020207214423/http://wwwlnukahivatrading.com/noni.htm (2002).

Website publication: "Noni Juice," www.tipsofallsorts.com/noni.html p. 1-11 (1999).

Website publication "Noni or Nonu Fruit," www.noni-nonu.com (1999).

Website publication "100% Pure Standardized Noni Juice," www.evitamins.com (1999).

Weil, A., "Alternatives," Northern Echo, Darlington, UK, p. 1-2 (2000).

Yamada et al., "Antibacterial Composition" Abstract (1984).

Younos et al., "Analgesic and Behavioural Effects of *Morinda-citrifolia*" Planta Medica 56(5):430-434 (1990).

Bennett et al., "Xanthones from Guttiferae" Phytochemistry vol. 28, No. 4, pp. 967-998 (1989).

Brock et al., "Biology of Microorganisms," 6th Ed. Prentice-Hall, Inc. p. 334 (1994).

Buckenhuskes et al., "Analytische Charakterisierung von pasteurisiertem Sauerkraut in Dosen" pp. 454-463 (1984).

Conquer et al., "Supplementation with quercetin markedly increases plasma quercetin concentration . . . " Journal of Nutrition, vol. 128, Iss. 3, pp. 593-597 (Mar. 1998).

Csiszar et al., "Extracts of Morinda . . . Exhibit Selective Anti-Tumor . . . " (Abstract) Proceedings of the American Association for Cancer Research, vol. 42 p. 634 (Mar. 2001).

Cushman et al. "Angiotensin Converting Enzyme Inhibitors: Evolution . . . " Angiotensin Converting Enzyme Inhibitors, Horovitz Ed., pp. 3-25, Urban & Schwarzenberg (1981).

Lee, "MorindaNet plans for e-commerce" New Straits Times, beginning p. 7, (Jun. 17, 1999).

"Angiotensin I-Converting Enzyme; ACE" Online Mendelian Inhereitance in Man, Johns Hopkins University Website Publication, (Mar. 3, 2004).

Singh et al., "Folk Medicine in Tonga: A Study on the Use of Herbal Medicines . . . " Journal of Ethnopharmacology 12 (1984) pp. 305-329.

Wang et al. "Cancer Preventive Effect of *Morinda citrifolia* (Noni)" Annals of the N.Y. Academy of Sciences pp. 161-168 (2001) 952.

Website publication "Tahitian Noni Skin Care Systems," www.nonidrink.com/skin_care.html (2002).

Website publication "Nature's Sunshine Products," wwww.synergeyworldwide.com/SG/products/productlines/products.aspx?product=SG4066 (Feb. 24, 2005).

Bain, J. "Secret World of Noni," Toronto Star, Toronto, Ontario: Aug. 6, 1999, p. 1 (pp. 1-5 of ProQuest).

Navarre, I "76 Ways to Use Noni Fruit Juice for your Better Health" Pride Publishing, Orem, Utah, (Apr. 2001), pp. 57-59, 81-83, and 119-124.

Guardia et al. "Anti-Inflammatory Properties of Plant Flavonoids. Effects of Rutin, Quercetin and Hesperidin on Adjuvant Arthritis in Rat." II Farmaco, 56, (2001) pp. 683-387.

Cimanga et al., Flavonoids 0-glycosides from Leaves of Morinda Morindoides, Phytochemistry, 1995, 38(5), pp. 1301-1303.

Website Publication, Indo World, Nature'salternative.com, (Jan. 1, 2001), http://www.indo-world.com/profile.htm.

Chye, K.T., "A Juice for Many Ailments," New Straits Times, Aug. 10, 1999, pp. 5 (pp. 1-3 of ProQuest direct).

Blanco et al. "The noni fruit (*Morinda citrifolia* L.): A review of agricultural research, nutritional and therapeutic properties," Journal of Food Composition and Analysis, 2006, vol. 19, pp. 645-654.

\* cited by examiner

ANTIVIRAL *MORINDA CITRIFOLIA* L. BASED FORMULATIONS AND METHODS OF ADMINISTRATION

RELATED APPLICATIONS

This application claims priority to provisional application Ser. No. 60/740,593 filed Nov. 29, 2005, entitled "Antiviral *Morinda Citrifolia* L. Based Formulations and Methods for Administration" and is a continuation-in-part of U.S. patent application Ser. No. 10/006,014 filed Dec. 4, 2001 now abandoned, entitled "Tahitian Noni Juice On Cox-1 And Cox-2 And Tahitian Noni Juice As A Selective Cox-2 Inhibitor", which claims priority to U.S. Provisional Patent Application Ser. No. 60/251,416 filed Dec. 5, 2000, entitled "Cox-1 and Cox-2 Inhibition Study on TNJ" and is a continuation-in-part of U.S. patent application Ser. No. 10/993,883, now U.S. Pat. No. 7,186,422 filed Nov. 19, 2004, entitled "Preventative And Treatment Effects Of *Morinda Citrifolia* On Diabetes And Its Related Conditions" which is a divisional of U.S. application Ser. No. 10/286,167, now U.S. Pat. No. 6,855,345 filed Nov. 1, 2002, entitled "Preventative And Treatment Effects Of *Morinda Citrifolia* On Diabetes And Its Related Conditions" which claims priority to U.S. Provisional Application Ser. No. 60/335,313, filed Nov. 2, 2001, and entitled, "Methods for Treating Conditions Related to Diabetes."

BACKGROUND

1. Field of Invention

The present invention relates to formulations for inhibiting Cathepsin G, Cathepsin S, Cathepsin B, Cathepsin L, Butyryl Cholinesterase, Peptidase HIV-1, and NF-kB comprising processed *Morinda citrifolia* products and methods for administering such.

2. Background

Aspartic peptidases have received enormous interest because of their significant roles in human diseases like involvement of renin in hypertension, cathepsin D in metastasis of breast cancer, β-Secretase in Alzheimer's Disease, plasmepsins in malaria, HIV-1 peptidase in acquired immune deficiency syndrome, and secreted aspartic peptidases in candidal infections. The HIV-1 peptidase is required for the replication and further infection by the virus. Effort has taken place for several years to understand the properties of this enzyme, because it has potential as a drug target to control HIV-1.

Elevated cathepsin enzyme activity in serum or the extracellular matrix is often related to a number of pathological conditions. Cathepsin-mediated diseases include: Alzheimer's, numerous types of cancer, autoimmune related diseases like arthritis and the accelerated breakdown of bone structure seen with osteoporosis. Up-regulated cathepsin B and L activity has been linked to several types of cancer. These include cancer of the colon, pancreas, ovaries, breast, lung and skin (melanoma). Up-regulation of cathepsin K has been shown un lung tumors. Increased cathepsin K activity has also been linked to degenerative bone diseases including osteoporosis and post-menopausal osteoporosis.

The cathepsins family contains members of the lysosomal cysteine protease, members of the serine protease (cathepsin A, G) and aspartic protease (cathepsin D, E). These enzymes exist in their processed form as disulfide-linked heavy and light chain subunits with molecular weights ranging from 20-35 kDa. Cathepsin C is the noted exception, existing as an oligomeric enzyme with a MW ~200 kDa. Initially synthesized as inactive zymogens, they are post-transitionally processed into their active configurations after passing through the endoplasmic reticulum and subsequent incorporation into the acidic environment of the lysosomes.

In resting cells, cytoplasmic location of the nuclear transcription factor NF-kB is bound by an inhibitory subunits IkB; binding of IkB effectively masks the nuclear localization sequences present on the P50 and P65 subunits of NF-kB, preventing nuclear translocation. It appears that upon cellular stimulation, a signal transduction pathway is activated leading to phosphorylation of key serine residues in the IkB polypeptide whereupon the NF-kB-IkB complex dissociates, IkB is rapidly degraded, and the unmasked nuclear localization signal allows NF-kB to translocate into nucleus and activate the transcription of specific genes. It is known that NF-kB regulates many proinflammatory and prothrombic factors produced by activated leukocytes. NF-kB represents a master regulator of inflammation and is, therefore, an attractive target for drug development.

SUMMARY OF THE INVENTION

Some embodiments relate to formulations for inhibiting Cathepsin G, Cathepsin S, Cathepsin B, Cathepsin L, Butyryl Cholinesterase, Peptidase HIV-1, and NF-kB comprising processed *Morinda citrifolia* products and methods for administering such.

Some embodiments provide a method of treating various diseases and ailments, which comprise administering to said mammal a processed *Morinda citrifolia* product selected from a group consisting of: extract from the leaves of *Morinda citrifolia*, leaf hot water extract, processed *Morinda citrifolia* leaf ethanol extract, processed *Morinda citrifolia* leaf steam distillation extract, *Morinda citrifolia* fruit juice, *Morinda citrifolia* extract, *Morinda citrifolia* dietary fiber, *Morinda citrifolia* puree juice, *Morinda citrifolia* puree, *Morinda citrifolia* fruit juice concentrate, *Morinda citrifolia* puree juice concentrate, freeze concentrated *Morinda citrifolia* fruit juice, *Morinda citrifolia* seeds, *Morinda citrifolia* seed extracts, extracts from defatted *Morinda citrifolia* seeds and evaporated concentration of *Morinda citrifolia* fruit juice.

The features and advantages may be realized and obtained by means of the instruments and combinations particularly pointed out in the appended claims. Furthermore, the features and advantages of the invention may be learned by the practice of the invention or will be obvious from the description, as set forth hereinafter.

BRIEF DESCRIPTION OF THE DRAWINGS

The foregoing and other features of the present invention will become more fully apparent from the accompanying drawings when considered in conjunction with the following description and appended claims. Although the drawings depict only typical embodiments of the invention and are thus, not to be deemed limiting of the invention's scope, the accompanying drawings help explain the invention in added detail.

DETAILED DESCRIPTION OF THE INVENTION

Figure 1:
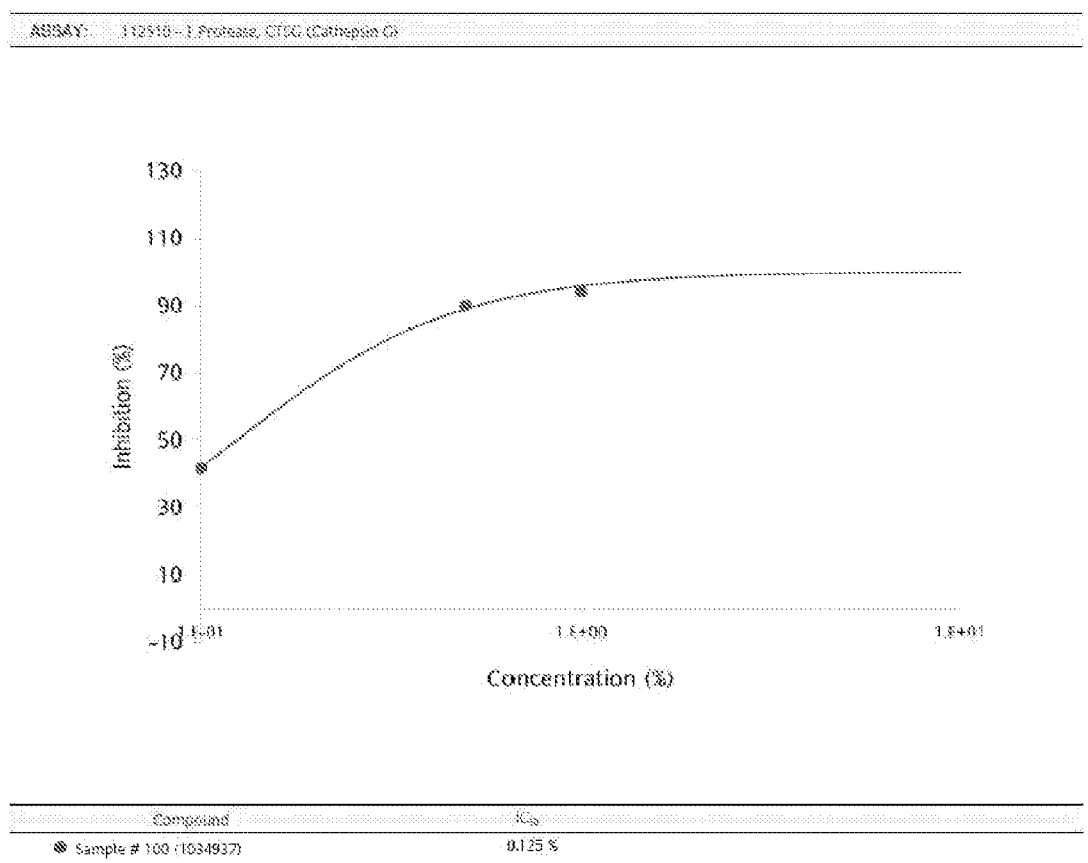
FIG. 1 illustrates percent inhibition of Cathepsin G by a concentrated *Morinda citrifolia* product.
Figure 2:
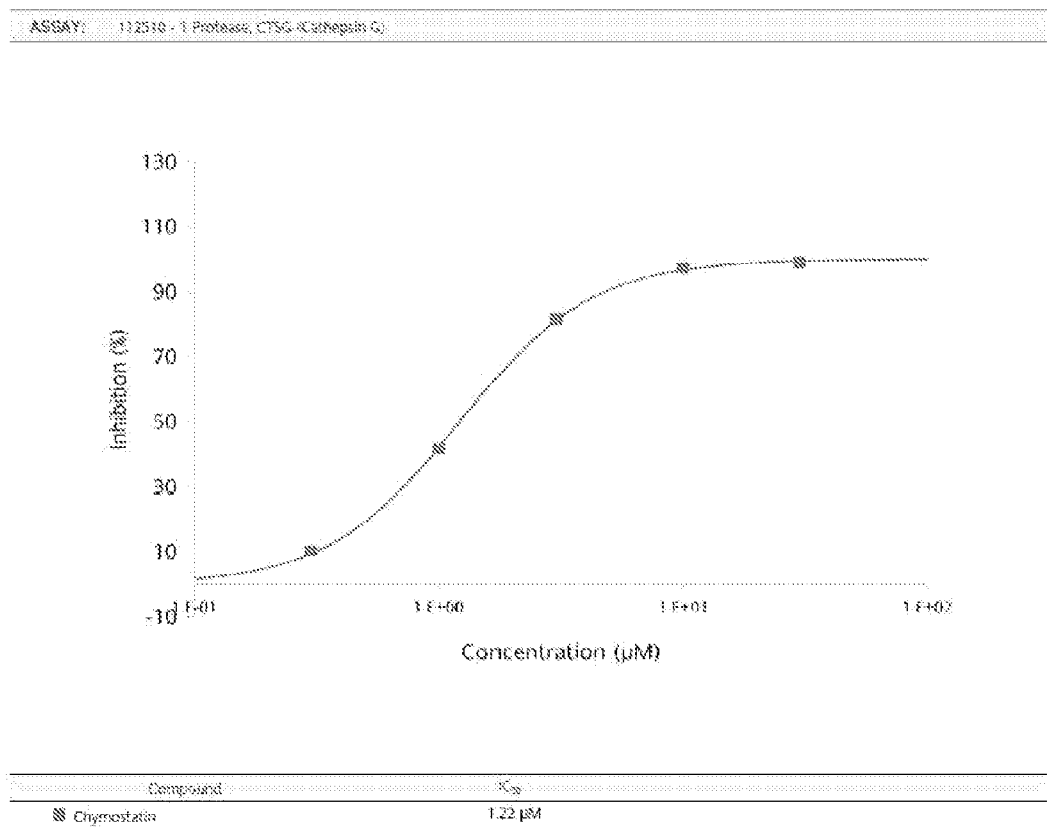
FIG. 2 illustrates percent inhibition of Cathepsin G by chymostatin.
Figure 3:
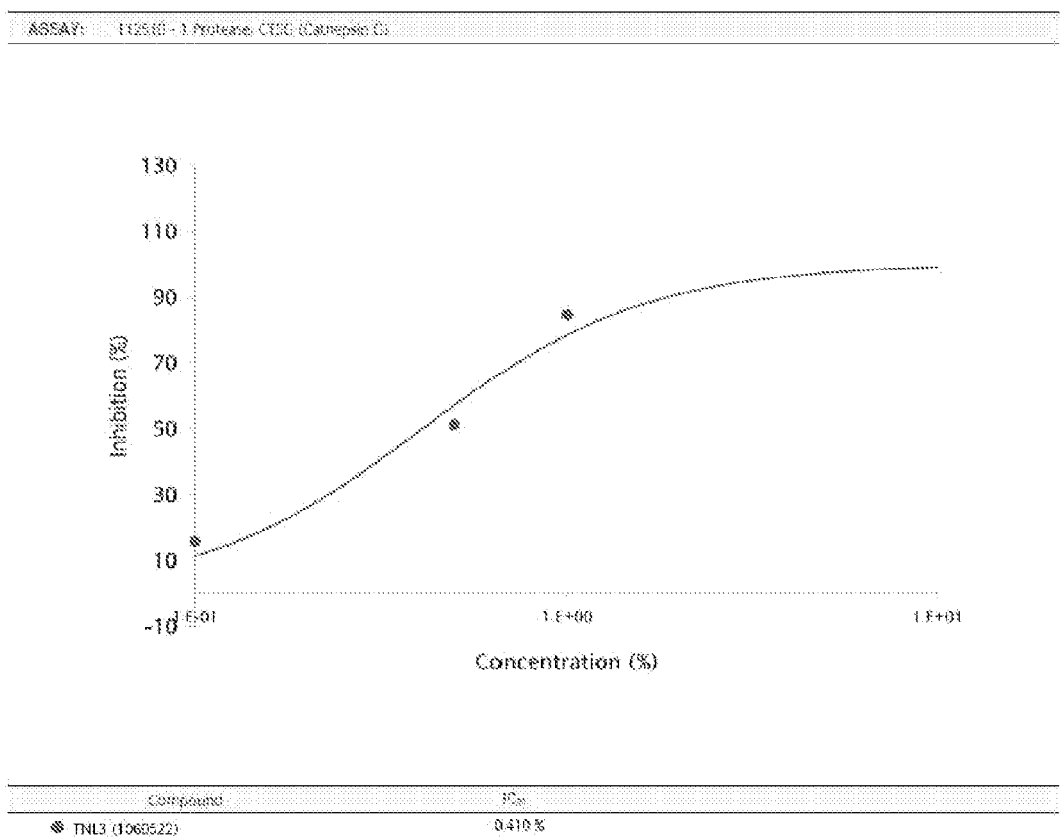
FIG. 3 illustrates percent inhibition of Cathepsin G by a processed *Morinda citrifolia* leaf fraction.
Figure 4:
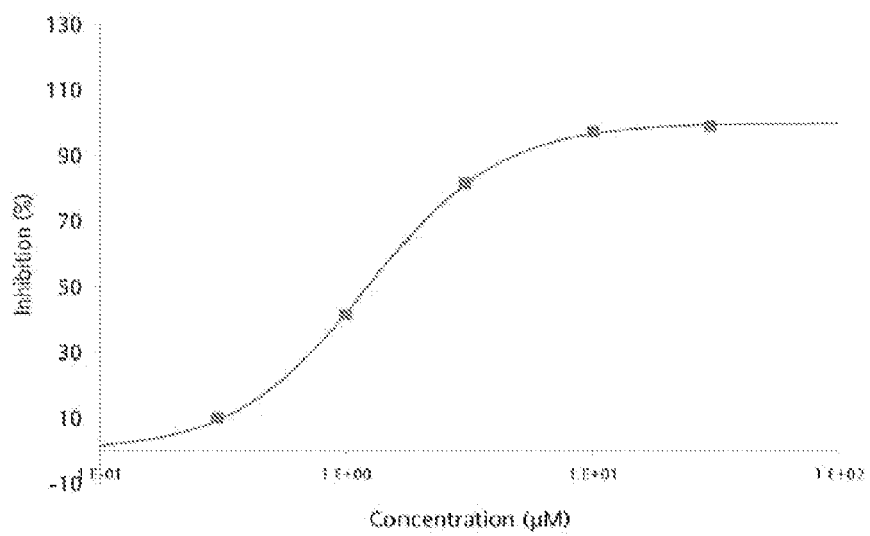
FIG. 4 illustrates percent inhibition of Cathepsin G by chymostatin.

It will be readily understood that the components of the present invention, as generally described herein, could be arranged and designed in a wide variety of different configurations. Thus, the following more detailed description of embodiments of the compositions and methods of the present invention is not intended to limit the scope of the invention, as claimed, but is merely representative of the presently preferred embodiments of the invention. The scope of the invention is, therefore, indicated by the appended claims rather than by the foregoing description. All changes that come within the meaning and range of equivalency of the claims are to be embraced within their scope.

Embodiments of the present invention feature methods and compositions for inhibiting Cathepsin G, Cathepsin S, Cathepsin B, Cathepsin L, Butyryl Cholinesterase, Peptidase HIV-1, and NF-kB comprising processed *Morinda citrifolia* products and to treat and prevent pathological conditions related to hypertension, metastasis of breast cancer, Alzheimer's Disease, acquired immune deficiency syndrome, candidal infections, numerous types of cancer, autoimmune related diseases like arthritis, accelerated breakdown of bone structure seen with osteoporosis, and inflammation. The foregoing list of ailments and diseases are mitigated, and the enzymatic inhibitions are fostered, through the administration of a composition comprising a component derived from the Indian Mulberry or *Morinda citrifolia* L. plant.

General Description of the *Morinda citrifolia* L. Plant

The Indian Mulberry or *Morinda citrifolia* plant, known scientifically as *Morinda Citrifolia* L. ("*Morinda citrifolia*"), is a shrub or small tree up to 10 m in height. The leaves are oppositely arranged with an elliptic to ovate form. The small white flowers are contained in a fleshy, globose, head like cluster. The fruits are large, fleshy, and ovoid. At maturity, they are creamy white and edible, but have an unpleasant taste and odor. The plant is native to Southeast Asia and has spread in early times to a vast area from India to eastern Polynesia. It grows randomly in the wild, and it has been cultivated in plantations and small individual growing plots. The *Morinda citrifolia* flowers are small, white, three to five lobed, tubular, fragrant, and about 1.25 cm long. The flowers develop into compound fruits composed of many small drupes fused into an ovoid, ellipsoid or roundish, lumpy body, with waxy, white, or greenish-white or yellowish, semi-translucent skin. The fruit contains "eyes" on its surface, similar to a potato. The fruit is juicy, bitter, dull-yellow or yellowish-white, and contains numerous red-brown, hard, oblong-triangular, winged 2-celled stones, each containing four seeds. When fully ripe, the fruit has a pronounced odor like rancid cheese. Although the fruit has been eaten by several nationalities as food, the most common use of the *Morinda citrifolia* plant has traditionally been as a red and yellow dye source.

Processing *Morinda citrifolia* Leaves

The leaves of the *Morinda citrifolia* plant are one possible component of the *Morinda citrifolia* plant that may be present in some compositions of the present invention. For example, some compositions comprise leaf extract and/or leaf juice as described further herein. Some compositions comprise a leaf serum that is comprised of both leaf extract and fruit juice obtained from the *Morinda citrifolia* plant. Some compositions of the present invention comprise leaf serum and/or various leaf extracts as incorporated into a nutraceutical product ("nutraceutical" herein referring to any drug or product designed to improve the health of living organisms such as human beings or mammals).

In some embodiments of the present invention, the *Morinda citrifolia* leaf extracts are obtained using the following process. First, relatively dry leaves from the *Morinda citrifolia* L. plant are collected, cut into small pieces, and placed into a crushing device—preferably a hydraulic press—where the leaf pieces are crushed. In some embodiments, the crushed leaf pieces are then percolated with an alcohol such as ethanol, methanol, ethyl acetate, or other alcohol-based derivatives using methods known in the art. Next, in some embodiments, the alcohol and all alcohol-soluble ingredients are extracted from the crushed leaf pieces, leaving a leaf extract that is then reduced with heat to remove all the liquid therefrom. The resulting dry leaf extract will herein be referred to as the "primary leaf extract."

In some embodiments of the present invention, the primary leaf extract is pasteurized to at least partially sterilize the extract and destroy objectionable organisms. The primary leaf extract is pasteurized preferably at a temperature ranging from 70 to 80 degrees Celsius and for a period of time sufficient to destroy any objectionable organisms without major chemical alteration of the extract. Pasteurization may also be accomplished according to various radiation techniques or methods.

In some embodiments of the present invention, the pasteurized primary leaf extract is placed into a centrifuge decanter where it is centrifuged to remove or separate any remaining leaf juice therein from other materials, including chlorophyll. Once the centrifuge cycle is completed, the leaf extract is in a relatively purified state. This purified leaf extract is then pasteurized again in a similar manner as discussed above to obtain a purified primary leaf extract.

Preferably, the primary leaf extract, whether pasteurized and/or purified, is further fractionated into two individual fractions: a dry hexane fraction, and an aqueous methanol fraction. This is accomplished preferably via a gas chromatograph containing silicon dioxide and CH2Cl2-MeOH ingredients using methods well known in the art. In some embodiments of the present invention, the methanol fraction is further fractionated to obtain secondary methanol fractions. In some embodiments, the hexane fraction is further fractionated to obtain secondary hexane fractions.

One or more of the leaf extracts, including the primary leaf extract, the hexane fraction, methanol fraction, or any of the secondary hexane or methanol fractions may be combined with the fruit juice of the fruit of the *Morinda citrifolia* plant to obtain a leaf serum (the process of obtaining the fruit juice to be described further herein). In some embodiments, the leaf serum is packaged and frozen ready for shipment; in others, it is further incorporated into a nutraceutical product as explained herein.

Processing *Morinda citrifolia* Fruit

Some embodiments of the present invention include a composition comprising fruit juice of the *Morinda citrifolia* plant. Because the *Morinda citrifolia* fruit is for all practical purposes inedible, the fruit must be processed in order to make it palatable for human consumption and included in the compositions of the present invention. Processed *Morinda citrifolia* fruit juice can be prepared by separating seeds and peels from the juice and pulp of a ripened *Morinda citrifolia* fruit; filtering the pulp from the juice; and packaging the juice. Alternatively, rather than packaging the juice, the juice can be immediately included as an ingredient in another product, frozen or pasteurized. In some embodiments of the present invention, the juice and pulp can be pureed into a homogenous blend to be mixed with other ingredients. Other processes include freeze drying the fruit and juice. The fruit and juice can be reconstituted during production of the final juice product. Still other processes may include air drying the fruit and juices prior to being masticated.

In a currently preferred process of producing *Morinda citrifolia* fruit juice, the fruit is either hand picked or picked by mechanical equipment. The fruit can be harvested when it is at least one inch (2-3 cm) and up to 12 inches (24-36 cm) in diameter. The fruit preferably has a color ranging from a dark green through a yellow-green up to a white color, and gradations of color in between. The fruit is thoroughly cleaned after harvesting and before any processing occurs.

The fruit is allowed to ripen or age from 0 to 14 days, but preferably for 2 to 3 days. The fruit is ripened or aged by being placed on equipment so that the fruit does not contact the ground. The fruit is preferably covered with a cloth or netting material during aging, but the fruit can be aged without being covered. When ready for further processing the fruit is light in color, such as a light green, light yellow, white or translucent color. The fruit is inspected for spoilage or for excessive green color and firmness. Spoiled and hard green fruit is separated from the acceptable fruit.

The ripened and aged fruit is preferably placed in plastic lined containers for further processing and transport. The containers of aged fruit can be held from 0 to 30 days, but preferably the fruit containers are held for 7 to 14 days before processing. The containers can optionally be stored under refrigerated conditions prior to further processing. The fruit is unpacked from the storage containers and is processed through a manual or mechanical separator. The seeds and peel are separated from the juice and pulp.

The juice and pulp can be packaged into containers for storage and transport. Alternatively, the juice and pulp can be immediately processed into a finished juice product. The containers can be stored in refrigerated, frozen, or room temperature conditions. The *Morinda citrifolia* juice and pulp are preferably blended in a homogenous blend, after which they may be mixed with other ingredients, such as flavorings, sweeteners, nutritional ingredients, botanicals, and colorings. The finished juice product is preferably heated and pasteurized at a minimum temperature of 181° F. (83° C.) or higher up to 212° F. (100° C.). Another product manufactured is *Morinda citrifolia* puree and puree juice, in either concentrate or diluted form. Puree is essentially the pulp separated from the seeds and is different than the fruit juice product described herein.

The product is filled and sealed into a final container of plastic, glass, or another suitable material that can withstand the processing temperatures. The containers are maintained at the filling temperature or may be cooled rapidly and then placed in a shipping container. The shipping containers are preferably wrapped with a material and in a manner to maintain or control the temperature of the product in the final containers.

The juice and pulp may be further processed by separating the pulp from the juice through filtering equipment. The filtering equipment preferably consists of, but is not limited to, a centrifuge decanter, a screen filter with a size from 1 micron up to 2000 microns, more preferably less than 500 microns, a filter press, a reverse osmosis filtration device, and any other standard commercial filtration devices. The operating filter pressure preferably ranges from 0.1 psig up to about 1000 psig. The flow rate preferably ranges from 0.1 g.p.m. up to 1000 g.p.m., and more preferably between 5 and 50 g.p.m. The wet pulp is washed and filtered at least once and up to 10 times to remove any juice from the pulp. The resulting pulp extract typically has a fiber content of 10 to 40 percent by weight. The resulting pulp extract is preferably pasteurized at a temperature of 181° F. (83° C.) minimum and then packed in drums for further processing or made into a high fiber product.

Processing *Morinda citrifolia* Seeds

Some *Morinda citrifolia* compositions of the present invention include seeds from the *Morinda citrifolia* plant. In some embodiments of the present invention, *Morinda citrifolia* seeds are processed by pulverizing them into a seed powder in a laboratory mill. In some embodiments, the seed powder is left untreated. In some embodiments, the seed powder is further defatted by soaking and stirring the powder in hexane—preferably for 1 hour at room temperature (Drug: Hexane—Ratio 1:10). The residue, in some embodiments, is then filtered under vacuum, defatted again (preferably for 30 minutes under the same conditions), and filtered under vacuum again. The powder may be kept overnight in a fume hood in order to remove the residual hexane.

Still further, in some embodiments of the present invention, the defatted and/or untreated powder is extracted, preferably with ethanol 50% (m/m) for 24 hours at room temperature at a drug solvent ratio of 1:2.

Processing *Morinda citrifolia* Oil

Some embodiments of the present invention may comprise oil extracted from the *Morinda Citrifolia* plant. The method for extracting and processing the oil is described in U.S. patent application Ser. No. 09/384,785, filed on Aug. 27, 1999 and issued as U.S. Pat. No. 6,214,351 on Apr. 10, 2001, which is incorporated by reference herein. The *Morinda citrifolia* oil typically includes a mixture of several different fatty acids as triglycerides, such as palmitic, stearic, oleic, and linoleic fatty acids, and other fatty acids present in lesser quantities. In addition, the oil preferably includes an antioxidant to inhibit spoilage of the oil. Conventional food grade antioxidants are preferably used.

Compositions and Their Use

The present invention features compositions and methods for inhibiting various enzymes comprising the administration of processed *Morinda citrifolia* based formulations.

The present invention also features compositions and methods for: ameliorating pathological conditions associated with Cathepsin G, Cathepsin S, Cathepsin B, Cathepsin L, Butyryl Cholinesterase, Peptidase HIV-1, and NF-kB. Embodiments of the present invention also comprise methods for internally introducing a *Morinda citrifolia* composition into the body of a mammal. Several embodiments of the *Morinda citrifolia* compositions comprise various different ingredients, each embodiment comprising one or more forms of a processed *Morinda citrifolia* component as taught and explained herein.

Compositions of the present invention may comprise any of a number of *Morinda citrifolia* components such as: extract from the leaves of *Morinda citrifolia*, leaf hot water extract, processed *Morinda citrifolia* leaf ethanol extract, processed *Morinda citrifolia* leaf steam distillation extract, *Morinda citrifolia* fruit juice, *Morinda citrifolia* extract, *Morinda citrifolia* dietary fiber, *Morinda citrifolia* puree juice, *Morinda citrifolia* puree, *Morinda citrifolia* fruit juice concentrate, *Morinda citrifolia* puree juice concentrate, freeze concentrated *Morinda citrifolia* fruit juice, *Morinda citrifolia* seeds,

*Morinda citrifolia* seed extracts, extracts taken from defatted *Morinda citrifolia* seeds, and evaporated concentration of *Morinda citrifolia* fruit juice. Compositions of the present invention may also include various other ingredients. Examples of other ingredients include, but are not limited to: artificial flavoring, other natural juices or juice concentrates such as a natural grape juice concentrate or a natural blueberry juice concentrate; carrier ingredients; and others as will be further explained herein.

Any compositions having the leaf extract from the *Morinda citrifolia* leaves, may comprise one or more of the following: the primary leaf extract, the hexane fraction, methanol fraction, the secondary hexane and methanol fractions, the leaf serum, or the nutraceutical leaf product.

In some embodiments of the present invention, active ingredients or compounds of *Morinda citrifolia* components may be extracted out using various procedures and processes commonly known in the art. For instance, the active ingredients may be isolated and extracted out using alcohol or alcohol-based solutions, such as methanol, ethanol, and ethyl acetate, and other alcohol-based derivatives using methods known in the art. These active ingredients or compounds may be isolated and further fractioned or separated from one another into their constituent parts. Preferably, the compounds are separated or fractioned to identify and isolate any active ingredients that might help to prevent disease, enhance health, or perform other similar functions. In addition, the compounds may be fractioned or separated into their constituent parts to identify and isolate any critical or dependent interactions that might provide the same health-benefiting functions just mentioned.

Any components and compositions of *Morinda citrifolia* may be further incorporated into a nutraceutical product (again, "nutraceutical" herein referring to any drug or product designed to improve the health of living organisms such as human beings or mammals). Examples of nutraceutical products may include, but are not limited to: intravenous products, topical dermal products, wound healing products, skin care products, hair care products, beauty and cosmetic products (e.g., makeup, lotions, etc.), burn healing and treatment products, first-aid products, antibacterial products, lip balms and ointments, bone healing and treatment products, meat tenderizing products, anti-inflammatory products, eye drops, deodorants, antifungal products, arthritis treatment products, muscle relaxers, toothpaste, and various nutraceutical and other products as may be further discussed herein.

The compositions of the present invention may be formulated into any of a variety of embodiments, including oral compositions, topical dermal solutions, intravenous solutions, and other products or compositions.

Oral compositions may take the form of, for example, tablets, lozenges, aqueous or oily suspensions, dispersible powders or granules, emulsions, syrups, or elixirs. Compositions intended for oral use may be prepared according to any method known in the art, and such compositions may contain one or more agents such as sweetening agents, flavoring agents, coloring agents, and preserving agents. They may also contain one or more additional ingredients such as vitamins and minerals, etc. Tablets may be manufactured to contain one or more *Morinda citrifolia* components in admixture with non-toxic, pharmaceutically acceptable excipients that are suitable for the manufacture of tablets. These excipients may be, for example, inert diluents, granulating and disintegrating agents, binding agents, and lubricating agents. The tablets may be uncoated or they may be coated by known techniques to delay disintegration and absorption in the gastrointestinal tract and thereby provide sustained action over a longer period. For example, a time delay material such as glyceryl monostearate or glyceryl distearate may be used.

Aqueous suspensions may be manufactured to contain the *Morinda citrifolia* components in admixture with excipients suitable for the manufacture of aqueous suspensions. Examples of such excipients include, but are not limited to: suspending agents such as sodium carboxymethyl-cellulose, methylcellulose, hydroxy-propylmethycellulose, sodium alginate, polyvinyl-pyrrolidone, gum tragacanth and gum acacia; dispersing or wetting agents such as a naturally-occurring phosphatide like lecithin, or condensation products of an alkylene oxide with fatty acids such as polyoxyethylene stearate, or condensation products of ethylene oxide with long chain aliphatic alcohols such as heptadecaethylene-oxycetanol, or condensation products of ethylene oxide with partial esters derived from fatty acids and a hexitol such as polyoxyethylene sorbitor monooleate, or condensation products of ethylene oxide with partial esters derived from fatty acids and hexitol anhydrides such as polyethylene sorbitan monooleate.

Typical sweetening agents may include, but are not limited to: natural sugars derived from corn, sugar beets, sugar cane, potatoes, tapioca, or other starch-containing sources that can be chemically or enzymatically converted to crystalline chunks, powders, and/or syrups. Also, sweeteners can comprise artificial or high-intensity sweeteners, some of which may include aspartame, sucralose, stevia, saccharin, etc. The concentration of sweeteners may be between from 0 to 50 percent by weight of the *Morinda citrifolia* composition, and more preferably between about 1 and 5 percent by weight.

Typical flavoring agents can include, but are not limited to, artificial and/or natural flavoring ingredients that contribute to palatability. The concentration of flavors may range, for example, from 0 to 15 percent by weight of the *Morinda citrifolia* composition. Coloring agents may include food-grade artificial or natural coloring agents having a concentration ranging from 0 to 10 percent by weight of the *Morinda citrifolia* composition.

Typical nutritional ingredients may include vitamins, minerals, trace elements, herbs, botanical extracts, bioactive chemicals, and compounds at concentrations from 0 to 10 percent by weight of the *Morinda citrifolia* composition. Examples of vitamins include, but are not limited to, vitamins A, B1 through B12, C, D, E, Folic Acid, Pantothenic Acid, Biotin, etc. Examples of minerals and trace elements include, but are not limited to, calcium, chromium, copper, cobalt, boron, magnesium, iron, selenium, manganese, molybdenum, potassium, iodine, zinc, phosphorus, etc. Herbs and botanical extracts may include, but are not limited to, alfalfa grass, bee pollen, chlorella powder, Dong Quai powder, Echinacea root, Gingko Biloba extract, Horsetail herb, Indian mulberry, Shitake mushroom, spirulina seaweed, grape seed extract, etc. Typical bioactive chemicals may include, but are not limited to, caffeine, ephedrine, L-carnitine, creatine, lycopene, etc.

The ingredients to be utilized in a topical dermal product may include any that are safe for internalizing into the body of a mammal and may exist in various forms, such as gels, lotions, creams, ointments, etc., each comprising one or more carrier agents. The ingredients or carrier agents incorporated into systemically (e.g., intravenously) administered compositions may also comprise any known in the art.

In one exemplary embodiment, a *Morinda citrifolia* composition of the present invention comprises one or more of a processed *Morinda citrifolia* component present in an amount by weight between about 0.01 and 100 percent by weight, and preferably between 0.01 and 95 percent by weight. Several embodiments of formulations are included in U.S. Pat. No. 6,214,351, issued on Apr. 10, 2001. However, these compositions are only intended to be exemplary, as one ordinarily skilled in the art will recognize other formulations or compositions comprising the processed *Morinda citrifolia* product.

In another exemplary embodiment, the internal composition comprises the ingredients of: processed *Morinda citrifolia* fruit juice or puree juice present in an amount by weight between about 0.1-80 percent; processed *Morinda citrifolia* oil present in an amount by weight between about 0.1-20 percent; and a carrier medium present in an amount by weight between about 20-90 percent. *Morinda citrifolia* puree juice or fruit juice may also be formulated with a processed *Morinda citrifolia* dietary fiber product present in similar concentrations.

EXAMPLES

The following examples illustrate some of the embodiments of the present invention comprising the administration of a composition comprising components of the Indian Mulberry or *Morinda citrifolia* L. plant. These examples are not intended to be limiting in any way, but are merely illustrative of benefits, advantages, and remedial effects of some embodiments of the *Morinda citrifolia* compositions of the present invention.

As illustrated by the following Examples, embodiments of the present invention have been tested against Cathepsin G, Cathepsin S, Cathepsin B, Cathepsin L, Butyryl Cholinesterase, Peptidase HIV-1, and NF-kB. Specifically, the -Example illustrate the results of in-vitro studies that confirmed that concentrates of processed *Morinda citrifolia* products ("TNJ" is an evaporative concentrate, "TNCONC" is a freeze concentrate, Noni Puree is a *Morinda citrifolia* based puree produced as described in this invention, Sample 100 is a Noni concentrate and NLF3 is Noni leaf active fractions) could have productive affects on various enzymes related to pathological conditions. The percentage of concentration refers to the concentration strength of the particular concentrate tested; that is, the strength of concentration relative to the processed *Morinda citrifolia* product from which the concentrate was obtained.

Example 1

All Cathepsin G inhibition assays described in Example 1 were conducted utilizing the protocol outlined in Table 1 and Table 2 below;

TABLE 1

Protease, CTSG (Cathepsin G)

| | |
|---|---|
| Source: | Human neutrophil |
| Substrate: | 20 μM Suc-Ala—Ala-Pro-Phe-AMC |
| Vehicle: | 1% DMSO |
| Pre-Incubation Time/Temp: | 15 minutes @ 25° C. |
| Incubation Time/Temp: | 30 minutes @ 25° C. |
| Incubation Buffer: | 50 mM $CH_3COONa$, pH 5.5, 1 mM DTT, 2 mM EDTA |
| Quantitation Method: | Spectrofluorimetric quantitation of AMC |
| Significance Criteria: | ≥50% of max stimulation or inhibition |

TABLE 2

REFERENCE COMPOUND DATA-BIOCHEMICAL ASSAYS

| Assay Name | Reference Compound | Historical $IC_{50}$ $K_I$ $n_H$ | Concurrent MIC $IC_{50}$ |
|---|---|---|---|
| Protease, CTSG (Cathepsin G) | Chumostatin | 2.1 μM | 1.22 μM |

Results of the assays reformed are illustrated in tables 3-5 and FIG. 1-4.

TABLE 3

| Compound | Species | Conc. | % INH. | $IC_{50}$ |
|---|---|---|---|---|
| Protease, CTSG (Cathepsin G) | | | | |
| Sample #100 | Hum | 0.5% | 90 | 0.125% |
| TNCMP1 | Hum | 0.1% | 98 | <0.1% |
| TNL3 | Hum | 0.5% | 51 | 0.410% |

TABLE 4

| Compound | Species | Conc. | % INH. | $IC_{50}$ |
|---|---|---|---|---|
| Protease, CTSG (Cathepsin G) | | | | |
| TNCMP1 | Hum | 0.1% | 98 | <0.1% |
| Sample #100 | Hum | 0.5% | 90 | 0.125% |
| TNL3 | Hum | 0.5% | 51 | 0.410% |

TABLE 5

| Compound Code | Batch* | SPP. | N = | CONC. | % | $IC_{50}$ |
|---|---|---|---|---|---|---|
| Protease, CTSG (Cathpsin G) | | | | | | |
| Sample #100 | 140236 | hum | 2 | 1% | 94 | 0.125% |
| | | | 2 | 0.5% | 90 | |
| | | | 2 | 0.1% | 42 | |
| TNCMP1 | 140236 | hum | 2 | 1% | 103 | <0.1% |
| | | | 2 | 0.5% | 101 | |
| | | | 2 | 0.1% | 98 | |
| TNL3 | 140236 | hum | 2 | 1% | 85 | 0.41% |
| | | | 2 | 0.5% | 51 | |
| | | | 2 | 0.1% | 16 | |

Example 2

Example 2 illustrates inhibition assays conducted on Cathepsins, Cathepsin B and Cethepsin L. the Example illustrate the results of in-vitro studies that confirmed that concentrates of processed *Morinda citrifolia* products ("TNJ" is an evaporative concentrate, "TNCONC" is a freeze concentrate, Noni Puree is a *Morinda citrifolia* based puree produced as described in this invention, Sample 100 is a Noni concentrate and NLF3 is Noni leaf active fractions) could have productive affects on various enzymes related to pathological conditions. The percentage of concentration refers to the concentration strength of the particular concentrate tested; that is, the strength of concentration relative to the processed *Morinda citrifolia* product from which the concentrate was obtained.

TABLE 6

| 112750 Peptidase, CTSS (Cathepsin S) | | | | | |
|---|---|---|---|---|---|
| Sample #100 | hum | 2 | 10% | 103 | <1% |
| | | 2 | 5% | 102 | |
| | | 2 | 1% | 90 | |
| TNCMP1 | hum | 2 | 10% | 110 | <1% |
| | | 2 | 5% | 128 | |
| | | 2 | 1% | 112 | |
| 112250 Protease, CTSB (Cathepsin B) | | | | | |
| Sample #100 | hum | 2 | 10% | 97 | 1.52% |
| | | 2 | 5% | 77 | |
| | | 2 | 1% | 38 | |
| TNCMP1 | hum | 2 | 10% | 110 | 1.31% |
| | | 2 | 5% | 77 | |
| | | 2 | 1% | 0 | |
| 112650 Protease, CTSL (Cathepsin L) | | | | | |
| Sample #100 | hum | 2 | 10% | 88 | 1.7% |
| | | 2 | 5% | 73 | |
| | | 2 | 1% | 37 | |
| TNCMP1 | hum | 2 | 10% | 100 | <1% |
| | | 2 | 5% | 100 | |
| | | 2 | 1% | 99 | |

All Assays performed illustrate the capacity of isolate products to inhibit Cathepsin.

Example 3

All Butyryl Cholinesterase and HIV-1 Protease assays described in Example 3 were conducted utilizing the protocol outlined in Table 7-9 below.

TABLE 7

| 104050 Cholinesterase, Butyryl, CHLE | |
|---|---|
| Source: | Human serum |
| Substrate: | 560 μM S-butyrylthiocholine |
| Vehicle: | 1% DMSO |
| Pre-Incubation Time/Temp: | 15 minutes @ 25° C. |
| Incubation Time/Temp: | 2 hours @ 25° C. |
| Incubation Buffer: | 0.1 M $Na_2HPO_4$, pH 7.4, 0.5% Tween 20 |
| Quantitation Method: | Spectrofluorimetric quantitation of thiocholine |
| Significance Criteria: | ≥50% of max stimulation or inhibition |

TABLE 8

| 113700 Peptidase, HIV-1 Protease | |
|---|---|
| Source: | Virus recombinant *E. coli* |
| Substrate: | 30 μM Anthranilyl-HIV protease substrate |
| Vehicle: | 1% DMSO |
| Pre-Incubation Time/Temp: | 15 minutes @ 25° C. |
| Incubation Time/Temp: | 5 minutes @ 25° C. |
| Incubation Buffer: | 0.1 M $CH_2COONa$, pH 4.7, 300 mM NaCl, 4 mM EDTA |
| Quantitation Method: | Spectrofluorimetric quantitation of Anthranilyl-tripeptides |
| Significance Criteria: | ≥50% of max stimulation or inhibition |

TABLE 9

| Reference Compound Data-Biochemical Assays | | | |
|---|---|---|---|
| Assay Name | Reference Compound | Historical $IC_{50} K_I n_H$ | Concurrent MIC $IC_{50}$ |
| Cholinesterase, Butyryl, CHLE | Physostigmine | 0.05 μM | 0.0772 μM |

TABLE 9-continued

| Reference Compound Data-Biochemical Assays | | | |
|---|---|---|---|
| Assay Name | Reference Compound | Historical $IC_{50} K_I n_H$ | Concurrent MIC $IC_{50}$ |
| Peptidase, HIV-1 Protease | Nelfinavir | 0.015 μM | 0.0267 μM |

Results are illustrated in tables 10-11 below. the Example illustrate the results of in-vitro studies that confirmed that concentrates of processed *Morinda citrifolia* products ("TNJ" is an evaporative concentrate, "TNCONC" is a freeze concentrate, Noni Puree is a *Morinda citrifolia* based puree produced as described in this invention, Sample 100 is a Noni concentrate and NLF3 is Noni leaf active fractions) could have productive affects on various enzymes related to pathological conditions. The percentage of concentration refers to the concentration strength of the particular concentrate tested; that is, the strength of concentration relative to the processed *Morinda citrifolia* product from which the concentrate was obtained.

TABLE 10

| Compound | Species | Conc. | % INH. |
|---|---|---|---|
| Peptidas, HIV-1 Protease | | | |
| Sample #100 | Vir | 1% | 60 |
| TNCMP1 | Vir | 1% | 117 |

TABLE 11

| Compound Code | Batch* Spp. | N = | Conc. | % |
|---|---|---|---|---|
| Cholinesterase, Butyryl, CHLE | | | | |
| TNCONC | hum | 2 | 5% | 38 |
| | | 2 | 1% | 14 |
| Sample #100 | hum | 2 | 5% | 23 |
| | | 2 | 1% | 9 |
| 113700 Peptidase, HIV-1 Protease | | | | |
| Sample #100 | vir | 2 | 5% | 108 |
| | | 2 | 1% | 60 |
| TNCMP1 | vir | 2 | 5% | 125 |
| | | 2 | 1% | 117 |

Example 4

Various *Morinda citrifolia* products were used in transcription response assays against human NF-kB. Human T lymphocytic Jurkat cells, transfected with a response element-lacZ reporter in which transcription of the β-galactosidase gene is directed by the binding site for the NF-kB transcription factor, are used. Test compound and/or vehicle is incubated with the cells (1.5×10/ml) in the presence of 0.5 uM A23187 and 50 ng/ml PMA (phorbol 12-myristate 13-acetate) in RPMI-1640 pH 7.4 at 37° C. for 4 hours. Test compound-induced β-galactosidase activity is determined by the convection of FDG (fluorescein di-β-D-galactopyranoside) to fluorescein. Fluorescence intensity is read on SpectroFluor Plus plate reader. Decrease of 50 percent or more (≥50%) in fluorescence intensity, relative to 10 uM cyclosporin A, indicates significant inhibitory activity. Compounds are screened at 10, 1, 0.1, 0.01 and 0.001 uM. These same concentrations are concurrently applied to a separate group of treated cells and evaluated for possible compound-induced cytotoxicity only if significant stimulation or inhibition is observed.

TABLE 12

Reference Compound Data-Cellular Assays

| Assay Name | Reference Compound | Historical IC$_{50}$/EC$_{50}$ | Concurrent MIC Batch* | IC$_{50}$/EC$_{50}$ |
|---|---|---|---|---|
| Transcription Response, NF-κB-Antagonist | Cyclosporin A | 0.05 μM | 109927 | 0.0372 μM |

All NF-kB assays described in Example 4 were conducted utilizing the protocol outlined above and in Tables 12-13.

TABLE 13

31600 Tranxription Response, NF-kB

| Target: | Human |
|---|---|
| Vehicle: | 0.4% DMSO |
| Incubation Time/Temp: | 4 hours @ 37° C. |
| Incubation Buffer: | RPMI-1640, 2 mM L-Glutamine, 10% FBS, pH 7.4 |
| Quantitation Method: | Spectrofluorimetric quantitation of fluorescein |
| Significance Criteria-Ag: | N/A |
| Significance Criteria-Ant: | ≥50% Decrease in A23187 + PMA-induced β-galactosidase expression relative to cyclosporin A |

Figure 5:
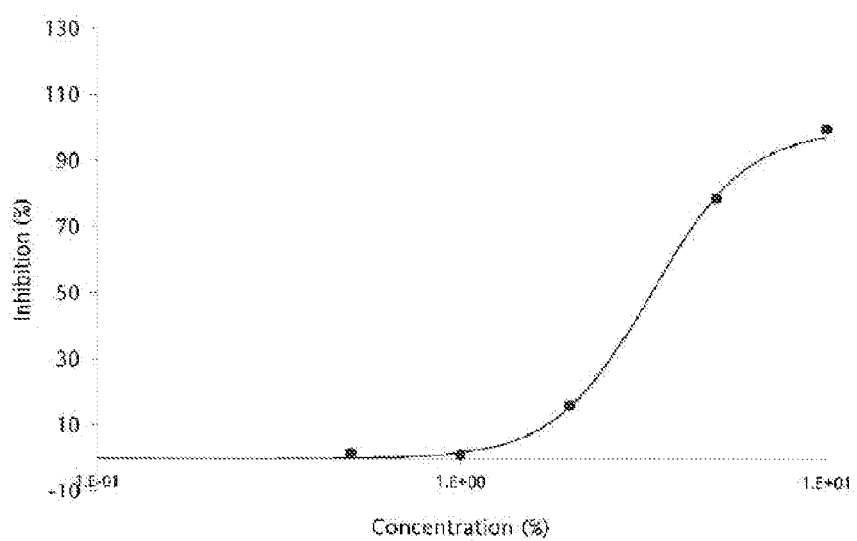
FIG. 5 illustrates the transcription response of NF-kB in the presence of TAHITIAN NONI® juice.
Figure 6:
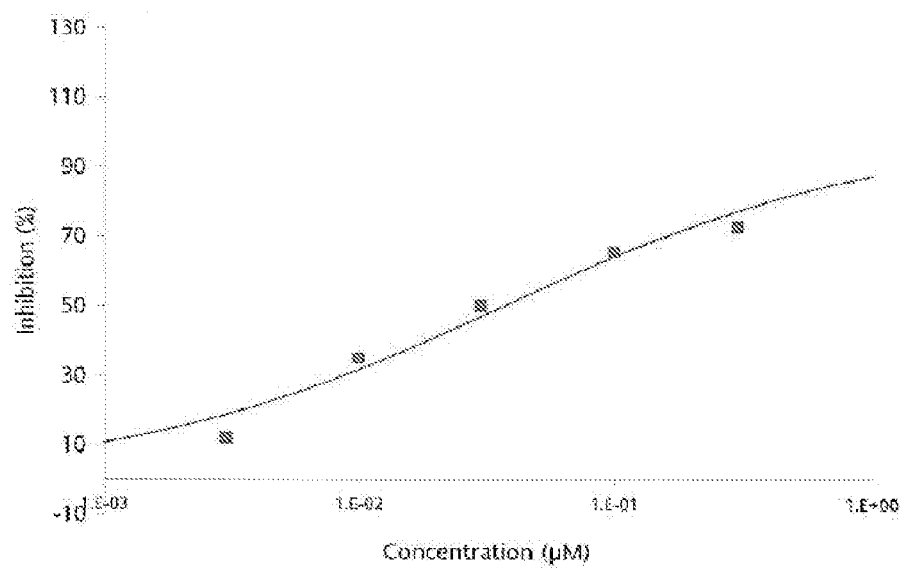
FIG. 6 illustrates the transcription response of NF-kB in the presence of Cyclosporin A.

Results from the Assays conducted are illustrated in Tables 14-15 and FIGS. 5 and 6.

TABLE 14

| Preliminary Cellular Assay | Species | Cell Name | Conc. | Criteria | % Response Resp. | Ag. | Ant. | EC$_{50}$/IC$_{50}$ |
|---|---|---|---|---|---|---|---|---|
| Transcription Response, NF-kB | Hum | | 5% | ≥=50% | | | 126 | 3.32% |

TABLE 15

Cellular Assays

| Assay Name | Tissue, Species | N = | Conc. | Criteria | % Response Resp. | Ag. | Ant. |
|---|---|---|---|---|---|---|---|
| Trancription Response, NF-kB | Hum | 2 | 10% | ≥±50% | | | 158 |
| | Hum | 2 | 5% | ≥±50% | | | 125 |
| | Hum | 2 | 2% | ≥±50% | | | 31 |
| | Hum | 2 | 1% | ≥±50% | | | 8 |
| | Hum | 2 | 0.5% | ≥±50% | | | 8 |

Example 5

Figure 7:
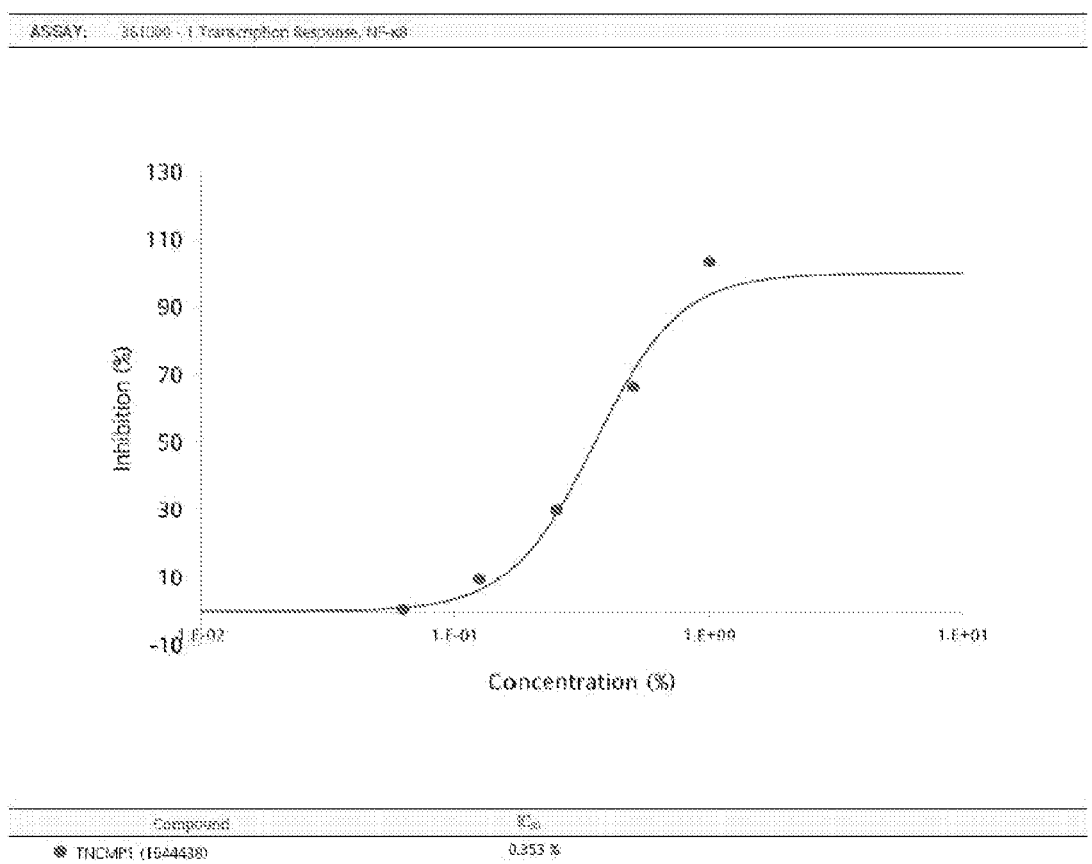
FIG. 7 illustrates percent the transcription response of NF-kB in the presence of a concentrated *Morinda citrifolia* product.
Figure 8:
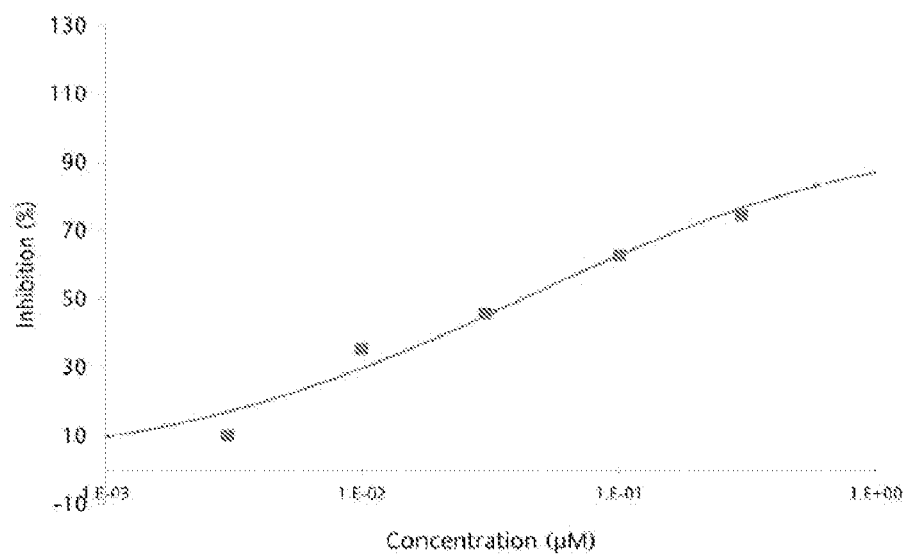
FIG. 8 illustrates percent the transcription response of NF-kB in the presence of Cyclosporin A.

All NF-kB assays described in Example 5 were conducted utilizing the protocol outlined above in EXAMPLE 4 and in Table 16. Results of the Assays conducted are illustrated in tables 16-18 and FIGS. 7 and 8.

TABLE 16

361000 Transcription Response, NF-kB

| Target: | Human |
|---|---|
| Vehicle: | 0.4% DMSO |
| Incubation Time/Temp: | 4 hours @ 37° C. |
| Incubation Buffer: | RPMI-1640, 10% FBS, 2 mM L-Glutamine, pH 7.4 |
| Quantitation Method: | Spectrofluorimetric quantitation of β-galactosidase |
| Significance Criteria-Ag.: | N/A |
| Significance Criteria-Ant: | ≥50% Decrease in A23187 + PMA-induced β-galactosidase expression relative to cyclosporine A |

TABLE 17

Reference Compound Data-Cellular Assays

| Assay Name | Reference Compound | Historical IC$_{50}$/EC$_{50}$ | Concurrent MIC Batch* | IC$_{50}$/EC$_{50}$ |
|---|---|---|---|---|
| Transcription Response, NF-kB-Antagonist | Cyclosporin A | 0.05 μM | 147828 | 0.0421 μM |

TABLE 18

| Primary Cellular Assay | Species | Cell Name | Conc. | Criteria | % Response Resp. | Ag. | Ant. | EC$_{50}$/IC$_{50}$ |
|---|---|---|---|---|---|---|---|---|
| Transcription Response, NF-kB | Hum | | 0.5% | ≥±50% | | | 66 | 0.353% |

TABLE 19

| | | Cellular Assays | | | | | % Response | |
|---|---|---|---|---|---|---|---|---|
| Assay Name | Batch* | Tissue, Species | N = | Conc. | Criteria | Resp. | Ag. | Ant. |
| Transcription Response, NF-kB | 147828 | Hum | 2 | 1% | ≥±50% | | | 103 |
| | 147828 | Hum | 2 | 0.5% | ≥±50% | | | 66 |
| | 147828 | Hum | 2 | 0.25% | ≥±50% | | | 30 |
| | 147828 | Hum | 2 | 0.125% | ≥±50% | | | 10 |
| | 147828 | hum | 2 | 0.0625% | ≥±50% | | | 1 |

The present invention may be embodied in other specific forms without departing from its spirit of essential characteristics. The described embodiments are to be considered in all respects only as illustrative and not restrictive. The scope of the invention is, therefore, indicated by the appended claims, rather than by the foregoing description. All changes that come within the meaning and range of equivalency of the claims are to be embraced within their scope.

What is claimed is:

1. A formulation for inhibiting at least one aspartic peptidase comprising:
   processed *Morinda citrifolia* fruit juice in an amount by weight between about 0.1-80%;
   processed *Morinda citrifolia* oil present in an amount by weight between about 0.1-20%; and
   a carrier medium present in an amount by weight between about 20-90 percent, wherein the formulation is formulated to include quercetin in an amount between about 0.01 and 10% by weight such that the formulation inhibits at least one aspartic peptidase when ingested by a human.

2. The formulation of claim 1, wherein the carrier medium includes one or more of grape juice, blueberry juice or apple juice.

3. The formulation of claim 1, further comprising another *Morinda citrifolia* product, wherein said processed *Morinda citrifolia* product comprises a processed *Morinda citrifolia* selected from a group consisting of: extract from the leaves of *Morinda citrifolia*, leaf hot water extract present in an amount by weight between about 0.1 and 50 percent, processed *Morinda citrifolia* leaf ethanol extract present in an amount by weight between about 0.1 and 50 percent, processed *Morinda citrifolia* leaf steam distillation extract present in an amount by weight between about 0.1 and 50 percent for inhibiting an enzyme selected from a list consisting of Cathepsin G, Cathepsin S, Cathepsin B, Cathepsin L, Butyryl Cholinesterase, Peptidase HIV-1, and NF-kB.

4. The formulation of claim 1, further comprising one or more nutritional ingredients in an amount by weight between about 0.1-10 percent, the nutritional ingredients comprising vitamins, minerals, trace elements, herbs, botanical extracts, and bioactive chemicals.

5. The formulation of claim 1, wherein said formulation further comprises an active ingredient Rutin present in an amount between about 0.1 and 10 percent by weight.

6. The formulation of claim 1, wherein said formulation is formulated for administering in a way selected from a list consisting of orally, topically, and intravenously.

* * * * *